United States Patent [19]

Task

[11] 4,249,823
[45] Feb. 10, 1981

[54] WINDSCREEN ANGULAR DEVIATION MEASUREMENT DEVICE

[75] Inventor: Harry L. Task, Dayton, Ohio

[73] Assignee: The United States of America as represented by the Secretary of the Air Force, Washington, D.C.

[21] Appl. No.: 85,453

[22] Filed: Oct. 16, 1979

[51] Int. Cl.³ ............................................. G01N 21/41
[52] U.S. Cl. .............................. 356/128; 250/237 G; 356/239
[58] Field of Search .................... 356/239, 128–137, 356/399–401; 250/237 G

[56] References Cited

U.S. PATENT DOCUMENTS 3,688,235  8/1972  Migeotte .............................. 356/239

Primary Examiner—John K. Corbin
Assistant Examiner—Bruce Y. Arnold
Attorney, Agent, or Firm—Donald J. Singer; Casimer K. Salys

[57] ABSTRACT

An apparatus for detecting the angular deviation from an axis imparted to a ray when passing through a transparent medium, for resolving the angular deviation into its components, and for generating electrical signals accurately representing the magnitudes of such components. A laser beam is projected along an optical axis through the medium and focussed by a displacement compensation lens. The beam is divided into channels with a beam splitter, each channel being incident upon a transmission diffraction grating. Each grating, characterized by fine parallel lines of substantially random size and spacing, generates a fan-shaped region of luminous energy. At a distance equal to the focal length of the lens, the fan-shaped regions cross detector arrays aligned parallel to the grating lines. A change in the angular deviation proportionally translates the crossing point along the detector array.

7 Claims, 4 Drawing Figures

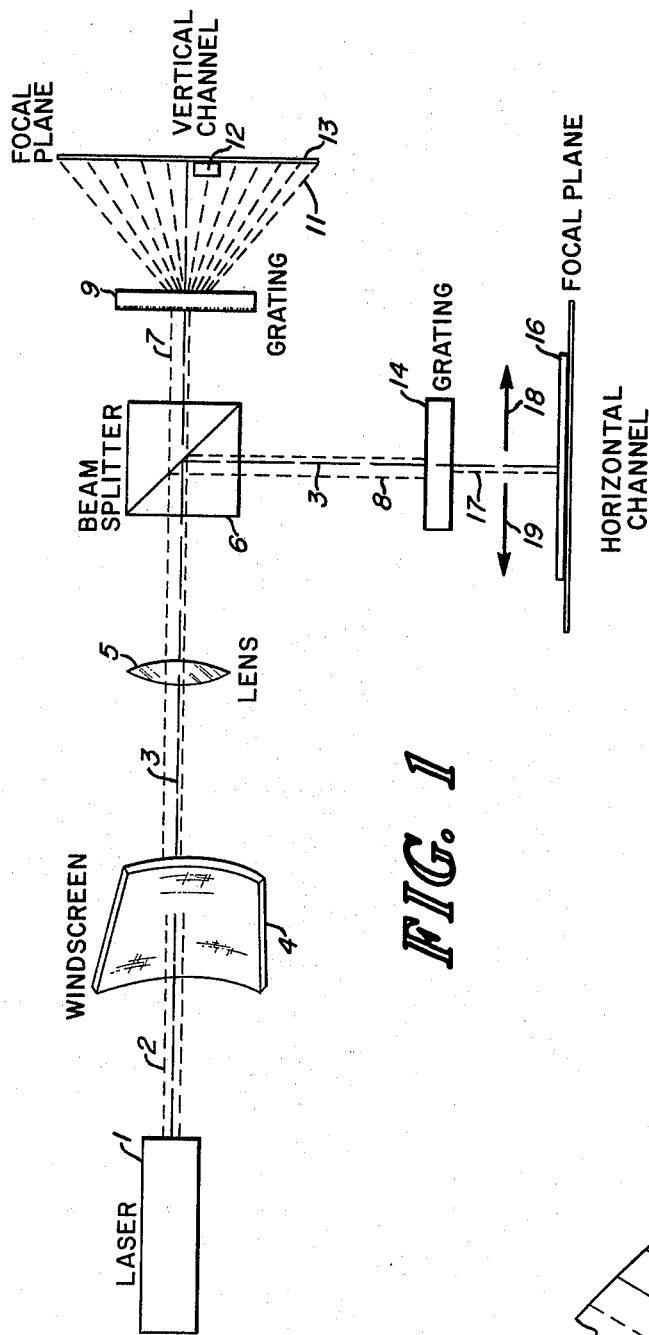
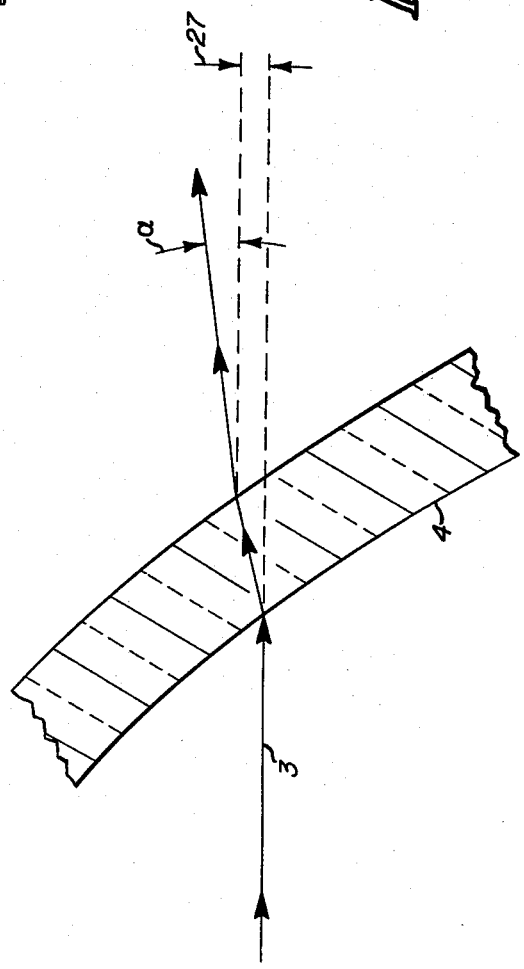

WINDSCREEN ANGULAR DEVIATION MEASUREMENT DEVICE

RIGHTS OF THE GOVERNMENT

The invention described herein may be manufactured and used by or for the Government of the United States for all governmental purposes without the payment of any royalty.

BRIEF SUMMARY

The present invention is directed to an apparatus for resolving, measuring and electrically sensing the components of angular deflection introduced when light rays pass through a distorting transparent medium. The apparatus is particularly suited for quantitatively ascertaining the degree of angular deviation type distortion introduced by windscreens or similar structures having complex curvilinear contours.

A laser beam is projected along an optical axis and through the transparent medium undergoing analysis. Upon passing through the medium, the beam is focussed with a displacement compensation lens and is divided into two independent channels by a beam splitter. Each of the beams created by the splitter is incident upon a diffraction grating having fine, parallel lines characterized by randomness in their placement and size. When the lines in the two gratings are oriented to be in perpendicular planes the angular deviation is resolved into its orthogonal components. A linear array of detectors for each channel is located in the focal plane of the lens, with consideration given for the effects of the intervening optical elements, and is longitudinally aligned to be parallel with the corresponding diffraction grating.

Upon passing through the transparent medium the laser beam is both displaced and angularly deflected from the optical axis as a result of distortions by the medium. The displacement effect is removed by the lens when the detector arrays are located at the focal plane.

The diffraction gratings in each channel of the split beam convert each beam incident thereon into a fan-shaped region of luminous energy, with the plane of the fan aligned perpendicular to the direction of the grating lines. An angular deviation in the plane of the grating lines is transformed into a proportional translation of the fan line. Since the fan line is aligned perpendicular to the linear array, and its intersection with array translates along the longitudinal axis of the array in proportion to the angular deviation of the beam, changes in the magnitude of angular deviation of the beam along predefined axes can be detected as incremental changes in the electric characteristic of the detectors in the array at the point of crossing.

DESCRIPTION OF THE DRAWINGS

FIG. 1 is a schematic of the complete apparatus for measuring angular deviation.

FIG. 3 schematically depicts the effects of distortion in a transparent medium on a ray passing therethrough.

DETAILED DESCRIPTION

Figure 2:
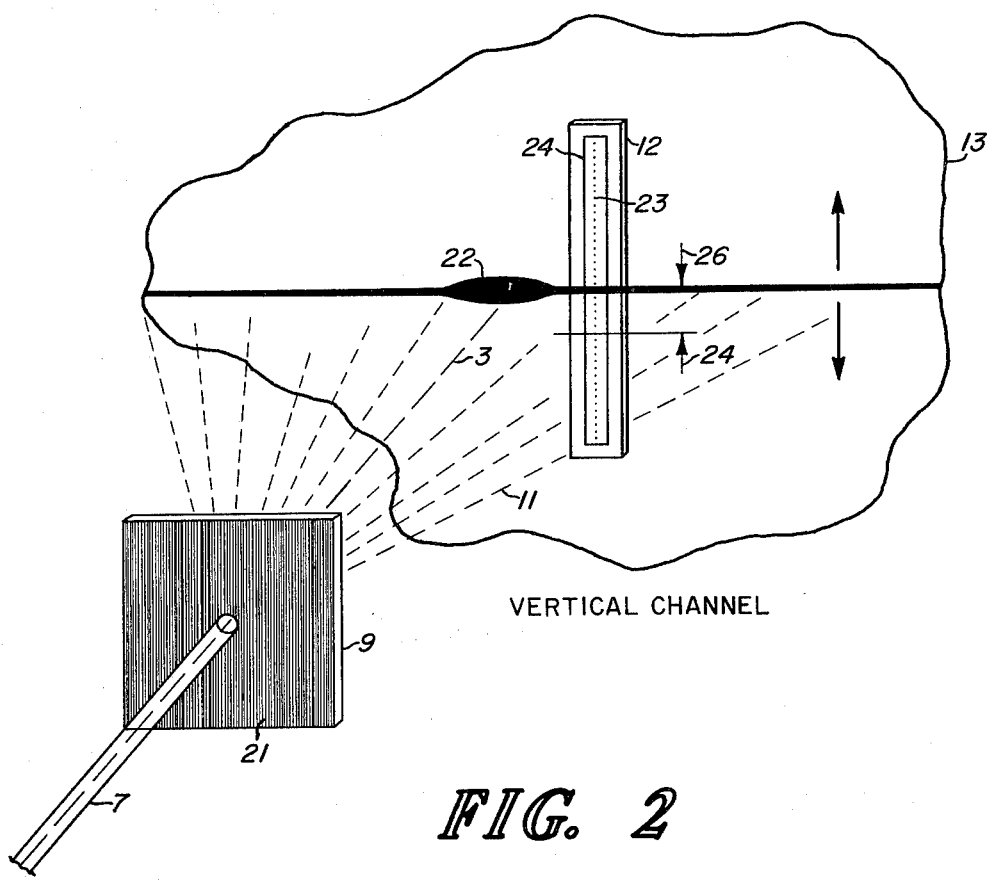
FIG. 2 is schematic in the perspective showing the vertical channel diffraction grating and detector array arrangement.

Measurement of the angular deviation imparted to a ray or beam of luminous energy as it passes through a transparent medium is very important if optical alignments are to be performed through the medium. An example, to which the invention embodiment is particularly directed, is the windscreen of an aircraft. If the observer inside the aircraft is to align any device within the aircraft to a target outside the aircraft, for instance a helmet mounted sight, that alignment must consider the effects of optical distortion introduced by the windscreen.

Since the displacement error between the true and distorted sight lines is generally small, and is unaltered by the range to the target, its effect is of limited concern. Angular deviation is otherwise, principally because the physical distance between the true and distorted lines of sight increases with the range to the target. The invention as embodied is directed toward measuring both the magnitude and direction of angular deviation distortion while suppressing the concurrent effects of displacement distortion.

In addition, the embodying apparatus measures angular deviation without the highly restrictive location and alignment requirements associated with devices presently available. An example of such apparatus appears in U.S. Pat. No. 3,688,235 to inventor Paul Migeotte. The attributes distinguishing both structure and operation will become apparent to one skilled in the art.

Attention is first directed to FIG. 1, where an embodiment of the apparatus is schematically depicted. As shown, laser 1 emits a narrow, collimated circular cross-section beam of luminous energy 2 centered about optical axis 3 which passes through windscreen 4. Though displaced and angularly deviated by windscreen distortion, the beam is incident on displacement compensation lens 5. The function, structure and location of the lens will be described with particularity hereinafter. Upon leaving lens 5 the beam is apportioned into two independent and substantially equal intensity channels by beam splitter 6. Though shown to be orthogonally oriented in the drawing, for purposes of generating vertical and horizontal channels, the invention is not so restricted. Since beams 7 and 8 are processed in a substantially identical manner, though rotated by 90 degrees, only one needs description.

Consider the vertical channel along the path of beam 7. As implied by its title the electrical signal derived represents the vertical component of the angular deviation caused by windscreen 4. In line with beam 7 is transmission diffraction grating 9, which for purposes of characterization has a multiplicity of randomly placed and sized, parallel grating lines, running perpendicular to the plane of the drawing sheet. Incident beam 7 is transformed by grating 9 into fan line 11 of luminous energy projecting in a plane parallel to the plane of the drawing. Linear array of detectors 12 lies in the focal plane of lens 4, with the location taking into account the optical effects of beam splitter 6 and grating 9. Since the longitudinal axis of linear array 12 is fixed to be in parallel with the grating lines, fan line 11 and array 12 cross at a single location. The translation of fan line 11 in proportion to the vertical component of angular deviation in windscreen 4 introduces a proportionate change in the crossing point along the face of array 12. As discrete elements in the array are illuminated their electrical response is indicative of angular deviation, which if calibrated provides a direct measure of the vertical component.

This phenomenon and other inherent characteristics are further illustrated in the perspective of FIG. 2. As noted previously, diffraction grating lines 21 produce fan line 11 when illuminated with laser beam 7 of substantially circular cross-section. The image of fan line 11 does contain a region, designated 22, on optical axis 3 having an intensity and width greater than the remainder of the image at plane 13. If array 12 were aligned with optical axis 3, expanded region 22 would simultaneously illuminate multiple array elements 23 through optical window 24. To avoid the loss in accuracy normally associated with this phenomenon, detector array 12 is shown displaced laterally to the right of the optical axis.

As was described previously, the vertical component of angular deviation is electronically ascertained by scanning the detectors. For instance, once calibrated a translation of the focused fan line between location 24 and new location 26, as a result of an interposed windscreen, provides a direct, incremental measure of angular deviation. It is worth noting that fan line 11 and expanded region 22 undergo lateral shifting as a result of horizontal deviations introduced into channel 7 of the laser beam. Nevertheless, the initial offset is sufficiently large to insure that expanded region 22 never illuminates array elements 23. Thus, all array elements 23 are subjected to fan line image of nearly equal width and intensity. Furthermore, since line locations 24 and 26 are electronically measured relative to each other, slight misalignments in the optical axes of the apparatus are automatically excluded from the measurement.

The operation of the horizontal channel shown in FIG. 1 is analogous, excepting that diffraction grating 14 and linear array 16 are rotated 90 degrees about axis 3. As in the vertical channel, horizontal channel fan line 17 translates back and forth, shown by arrows 18 and 19, over the sensing face of array 16 in proportion to the horizontal component of the angular deflection introduced by windscreen 4. Thus, both vertical and horizontal components are resolved into their constituent components and detected as incremental changes in two linear arrays.

Figure 4:
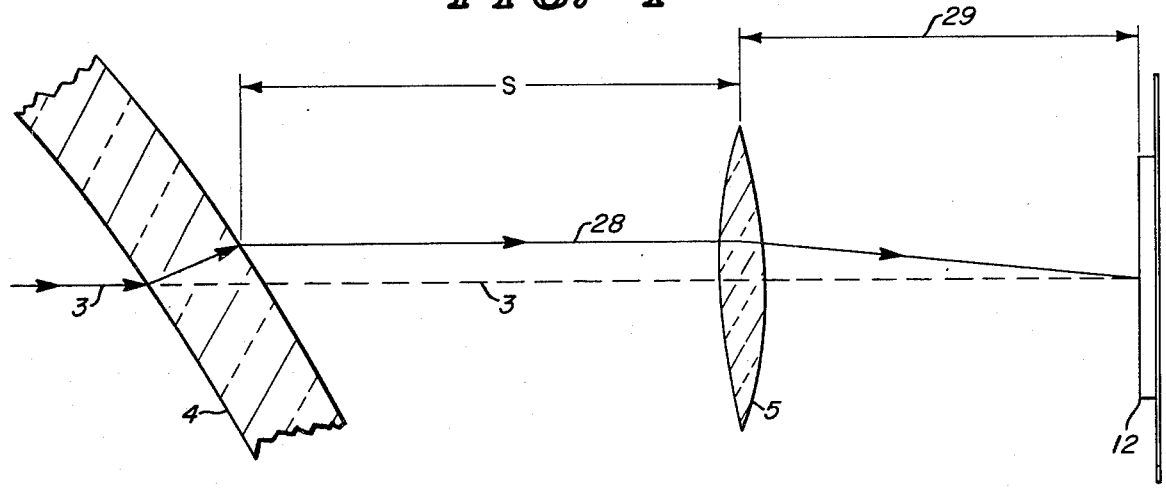
FIG. 4 schematically shows the method by which displacement effects are nullified.

The method by which displacement effects are suppressed is best explained with reference to the illustrations in FIGS. 3 and 4. As shown in FIG. 3 insertion of slightly distorted windscreen 4 imparts both a displacement, 27, and an angular deviation, α, to a ray of luminous energy traveling along optical path 3. Since angular deviation α is the parameter of principal concern, the displacement contribution is to be suppressed. Removal of displacement effect is accomplished as shown in FIG. 4, where the effects of angular deviation have been excluded for purposes of clarity. Since, by definition, all displacement contributions 28 are parallel to optical axis 3, their effects are nulled at the focal point of conventional focussing lens 5. Thus, the effects of displacement are removed by locating the detectors in array 12 at an optical distance, 29, equal to the focal length of the lens. The remaining effects in the path of the ray are attributable to angular deviation alone.

Those skilled in the art recognize that optical distance 29, between the rear principal plane of lens 5 and the detectors in array 12, must take into account the optical effects on focal point of intervening elements. For the embodiment depicted in FIG. 1, this includes beam splitter 6 and diffraction grating 9.

Similarly, the optical configuration must consider other conventional optical constraints. One such restriction relates to the aperture diameter of lens 5 in relation to the distance between transparent medium 4 and lens 5. In such cases it is understood that the maximum combination of displacement and angular deviation imparted to the laser beam from its normal position on the optical axis must not deflect the beam outside the periphery of lens 5. Mathmetically this constraint is described by the relationship:

$$(d + s \tan \alpha) \leq A/2$$

where
 d = the displacement
 s = the distance between windscreen 4 and lens 5 (see FIG. 4)
 A = the diameter of lens 5
 α = the angular deviation.

The relationship between the angular deviation and the distances translated by the focus of the fan line along the face of the linear array is also amenable to mathematical description. Using FIG. 2, the relationship is defined by:

$$\alpha = \arctan r/f$$

where
 α = the vertical component of angular deviation
 r = the distance between lines 24 and 26
 f = effective focal length of lens 5.

Though diffraction gratings 9 and 14 are susceptible to manufacture using highly refined techniques, the gratings in the embodiment were fabricated in simple fashion from transparent plastic sheets scratched on one side with sandpaper. However, during such fabrication care must be exercised to maintain uniform alignment and pressure during the scratching process, without creating a pattern of equal size and distribution. Uniformity of size and spacing creates a diffraction pattern with multiple, luminous energy spots in a line, while the invention here disclosed seeks a substantially uniform line of luminous energy.

It is worth noting that the apparatus disclosed resolves the angular deviation into its components along defined axes, rather than providing a mere vector amplitude whose direction is unknown. Furthermore, the axes are not restricted to an orthogonal orientation, but may, if the application demands, be aligned with planes of particular interest. Distinguishing further from the art, windscreen 4 is not highly constrained to a specific location between laser 1 and lens 5. This flexibility in the sample's location significantly eases the inspection of complex optical structures which have been permanently installed. The angular deviation measuring devices known by those practicing in the art as a general rule required exacting location of the transparent medium samples if angular deviation accuracy is to be maintained.

I claim:

1. An apparatus for measuring the angular deflection caused by a transparent medium, comprising:
   a. means for illuminating a test region of space with a laser beam projecting along an optical axis passing through said region;
   b. a transmission diffraction grating having fine, parallel lines of substantially random size and spacing, lying in a plane which is intersected by said optical axis;

c. a linear array of detectors responsive to laser luminous energy passing through said grating, lying in a plane substantially perpendicular to the optical axis and oriented to have its longitudinal axis parallel to the grating lines; and d. a displacement compensation lens, on the optical axis, at an optical distance corresponding to its focal length from the detector system.

2. The apparatus as recited in claim 1, wherein the linear array of detectors is displaced from the optical axis.

3. An apparatus for measuring the optical distortion caused by a transparent medium, comprising:

a. means for illuminating a test region of space with a laser beam; b. means for splitting said beam, after it has passed through said region, into first and second beam channels having first and second optical axes, respectively;

c. first means for diffracting said first beam channel into a first fan shaped region of luminous energy which, if projected onto a plane normal to said first optical axis, would form an illuminated area having a first line of symmetry;

d. second means for diffracting said second beam channel into a second fan shaped region of luminous energy which, if projected onto a plane normal to said second optical axis, would form an illuminated area having a second line of symmetry;

e. first means responsive to the luminous energy incident thereon, for detecting angular deviations of said laser beam caused by the insertion of said transparent medium into said test region, detecting the shift in the position of said first fan shaped region; and f. second means responsive to the luminous energy incident thereon, for detecting angular deviations of said laser beam caused by the insertion of said transparent medium into said test region, detecting the shift in the position of said second fan shaped region.

4. The apparatus as recited in claim 3, further including a displacement compensation lens, in the path of the laser beam, located so that the optical distance, from the lens to the means detecting shifts in said fan shaped regions, is equal to the focal length of the lens.

5. The apparatus as recited in claim 4, wherein the first and second means for diffracting the beam comprise transmission diffraction gratings having fine, parallel lines of substantially random size and spacing, and wherein the first and second means detecting shifts each comprise a linear array of detectors whose longitudinal axis is parallel to the grating lines.

6. The apparatus as recited in claim 5, wherein the diffraction gratings are orthogonally oriented and the shifts in the fan shaped regions are perpendicular to their respective lines of symmetry.

7. The apparatus as recited in claims 3, 4, 5 or 6 wherein said means detecting shifts are displaced from the optical axes of their respective beam channels.

* * * * *